United States Patent
Muuli et al.

(10) Patent No.: US 10,092,817 B2
(45) Date of Patent: Oct. 9, 2018

(54) SPORT POLE WITH SENSORS AND A METHOD FOR USING IT

(71) Applicants: Terje Muuli, Tallinn (EE); Kenneth Muuli, Tallinn (EE)

(72) Inventors: Terje Muuli, Tallinn (EE); Kenneth Muuli, Tallinn (EE)

( * ) Notice: Subject to any disclaimer, the term of this patent is extended or adjusted under 35 U.S.C. 154(b) by 0 days.

(21) Appl. No.: 15/555,113

(22) PCT Filed: Mar. 10, 2016

(86) PCT No.: PCT/EE2016/000002
§ 371 (c)(1),
(2) Date: Sep. 1, 2017

(87) PCT Pub. No.: WO2016/141947
PCT Pub. Date: Sep. 15, 2016

(65) Prior Publication Data
US 2018/0036624 A1    Feb. 8, 2018

(30) Foreign Application Priority Data
Mar. 11, 2015    (EE) .................................. 201500011

(51) Int. Cl.
*A63C 11/22*    (2006.01)
*A63B 69/18*    (2006.01)
(Continued)

(52) U.S. Cl.
CPC ............ *A63C 11/225* (2013.01); *A63B 69/18* (2013.01); *A45B 3/00* (2013.01); *A45B 3/08* (2013.01);
(Continued)

(58) Field of Classification Search
CPC ......... A45B 3/08; A45B 3/00; A63C 2203/18; A63C 11/221; A63C 11/225; A63C 11/228; G01B 11/026
See application file for complete search history.

(56) References Cited

U.S. PATENT DOCUMENTS

| 4,858,125 | A | * | 8/1989 | Washizuka | ............... | A45B 3/00 |
| | | | | | | 135/65 |
| 6,011,481 | A | * | 1/2000 | Luther | ..................... | A61H 3/02 |
| | | | | | | 135/66 |

(Continued)

FOREIGN PATENT DOCUMENTS

EP    1 908 499    *    9/2008

*Primary Examiner* — Emma K Frick
(74) *Attorney, Agent, or Firm* — W&C IP

(57) ABSTRACT

The present invention relates to a sport stick that measures the driving force generated by the upper body, which is applied to the ground through poles during the natural performance of nordic walking or any other sport, where poles are used to drive/propel the body forward. An inclination sensor along with a pole length sensor (pole length constant in a fixed length pole) has been placed into the pole for the achievement of the most suitable biomechanical performance, i.e. proper technique. The sport pole uses the Global Positioning System along with a topographical map to ensure that the slope of terrain does not affect the inclination sensor measurements. All collected data is analyzed by a control center, wherein correct usage models have been saved along with a collection of the user's anthropometric and fitness levels.

20 Claims, 5 Drawing Sheets

(51) Int. Cl.
  *A45B 3/08* (2006.01)
  *A63B 71/06* (2006.01)
  *A63B 69/00* (2006.01)
  *A61B 5/00* (2006.01)
  *A45B 3/00* (2006.01)
  *A63C 11/00* (2006.01)

(52) U.S. Cl.
  CPC ....... *A45B 2200/055* (2013.01); *A61B 5/6895* (2013.01); *A63B 71/0622* (2013.01); *A63B 2069/0031* (2013.01); *A63B 2069/0033* (2013.01); *A63B 2071/0691* (2013.01); *A63B 2220/18* (2013.01); *A63B 2220/51* (2013.01); *A63C 11/00* (2013.01); *A63C 11/221* (2013.01); *A63C 2203/18* (2013.01); *A63C 2203/24* (2013.01)

(56) References Cited

U.S. PATENT DOCUMENTS

| | | | |
|---|---|---|---|
| 7,066,864 B2* | 6/2006 | Olkkonen | A45B 3/08 135/65 |
| 7,959,539 B2* | 6/2011 | Takeishi | A63B 69/0028 377/24.2 |
| 8,612,181 B2* | 12/2013 | Czaja | A43B 3/0005 422/63 |
| 9,168,418 B2* | 10/2015 | Adamchick | A63B 71/0622 |
| 9,460,635 B2* | 10/2016 | Yu | G09B 21/003 |
| 9,618,624 B2* | 4/2017 | Krauss | A45B 3/08 |
| 9,675,515 B2* | 6/2017 | Chou | A45B 3/04 |
| 9,826,806 B2* | 11/2017 | Challa | A45B 9/02 |
| 9,872,811 B2* | 1/2018 | Yu | G09B 21/003 |
| 2005/0005467 A1* | 1/2005 | Hannel | G01B 5/12 33/542 |
| 2011/0131012 A1 | 6/2011 | Stanislaw et al. | |
| 2017/0211997 A1* | 7/2017 | Kulach | G01L 3/247 |

* cited by examiner

| Adjustable element | Increase | Decrease | At norm | Light signaling adjustment need |
|---|---|---|---|---|
| Pole length | LED3 (scale) | LED3 (scale) | LED6 (scale) | LED4 (scale) |
| Force applied to pole | LED2 (scale) | LED2 (scale) | LED7 | - |
| Inclination | LED5 (scale) | LED5 (scale) | LED6 | - |

FIG 3

SPORT POLE WITH SENSORS AND A METHOD FOR USING IT

TECHNICAL FILED

The present invention relates to sport poles (henceforth also "sport stick"), precisely nordic walking, skiing poles or any other sport practiced with poles, where the poles are used to achieve balance and propel the body forward during movement. More accurately, during this type of movement, based on information gathered and recorded in real-time, it is meant to help a user achieve correct technique, set exercise intensity, achieve exercise goals and convey detailed information about the user's upper-body activity and Sagittal plane strength balance to analyse the sport sticks user's development in an exercise, but sometimes also in a rehabilitation context.

BACKGROUND OF THE INVENTION

Poles, which are used for nordic walking (training and rehabilitation), skiing, roller skating etc., from both an exercise analysis and user friendliness advancing perspective, have been developed with sensors repeatedly. An example of such exercise analysis simplifying development is seen in the patent document WO 2003002218 A1. To an ordinary nordic walking or skiing pole a power sensor has been added to measure the force generated by the arms that transfers onto the ground. Based on that estimate calorie consumption and upper-body Sagittal plane strength balance can be measured. An example from both a training analysis and user friendliness advancing development is seen in the patent application EP 1908499 A1 filed in Europe. A collection of sensors have been added to the pole, that include but are not limited to an accelerometer inclination sensor and movement sensor. The sensor collection purpose is to, correspondingly to the field of application, save the correct technique and warn the user if their given technique deviates too far from the recorded model. A shortcoming of the sport poles described in the mentioned patent documents is that they do not provide the opportunity to set a user suitable pole length based on their training level. They also lack a pole length sensor, through which the pole receives information about its length.

The poles described in the previous documents also lack a GPS receiver, which, coupled with topographical maps, determines the pole inclination in relation to the ground, which in turn affects the sports' technical execution.

The poles described in the previous documents also lack the possibility to record necessary anthropometric (hand-, foot-, body length, weight etc.) and physiological (strength, age, traumas etc.) user information and user health protecting and technical execution measurement optimizing methodology to measure a user's real technical performance and to guide them towards correct technique via the sport poles signal lights.

This invention is aimed at solving all of those drawbacks.

SUMMARY OF THE INVENTION

Need for a person's biomechanics and its individual differences considering, real-time execution info gathering sport pole exists. Also, this several sensor equipped pole must be able to consider environmental factors like ground inclination affecting the sensors' readings.

One of the invention's aims is to precisely measure the force applied to the ground, propelling the person forward during execution, where the person's height, weight, maximum strength, age, trauma history and training level (henceforth together known as "user info"), also ground inclination and the poles' own length. These attributes are important, because otherwise the sensor info analysing and parameter model generating control center cannot take into account the differences derived from the user info, pole length, ground inclination and the dependent force application angle.

For example the often used adjustable nordic walking or trekking poles might have been adjusted to different lengths, because of which the force applied to them is remarkably different and potentially harmful to the bodies musculature structure and joints. The data analysing control centre interprets this, due to lacking information, as a significant upper-body limb strength difference and notifies the user accordingly, but the actual deviation from the correct model is caused by different pole length.

Another aim of the invention is correct technique assessment during execution, which means comparing the inclination sensor's measured inclination range, which considers ground inclination, and the force applied to the pole with a premade model. However, as an example, in case of nordic walking, if the control center does not know that the pole being used is too long for a person's anthropometric measurements then the inclination range can only be correct if they bring their hands in front of their body. This however contradicts the correct nordic walking technique, which mimics normal walking, and causes tension in a person's shoulder and back muscles and upper-body limb tendons.

From a technological standpoint a sport pole has been developed that includes a force sensor, either a spring scale or a strain gauge that instead of measuring weight will be set up to measure the muscle generated pressure applied to them when the poles are touching the ground, and inclination sensor, preferrably but not limited to an accelerometer inclination sensor, along with a pole length sensor, preferrably but not limited to a laser rangefinder inside the pole pointing down the shaft from one end to the other, and a Global Positioning System receiver (henceforth GPS), that works in co-operation with topographical maps, to accurately understand the inclination sensor readings that might be affected due to the different techniques used to ascend or descend terrain with sport poles, and user recorded user info. All results are analysed by and communicated to a user by the control center.

The control center has been set up so that according to the data from the inclination sensor that takes into account the ground inclination, about the hand movement angle range it directs a user to adjust the sport stick to a shorter or longer length after analysing the info in relation to the user height and trauma history. After achieving optimal hand movement range the control center communicates data about upper-body activity and Sagittal plane strength balance to the user, taking into consideration their body mass index and maximum strength and the individual usage model differences derived from them.

These and other parts, features, aspects and advantages of the given sport pole will become clear to an expert of the field in the following detailed description, which with the added figures reveals the preferred embodiment of the invention.

BRIEF DESCRIPTION OF THE DRAWINGS

The invention's aforementioned and other properties and advantages will be described in more detail below with reference to attached figures, which illustrate preferred embodiments, where.

FIG. 3 shows an example diagram of a signal light based user feedback system;

DETAILED DESCRIPTION OF THE INVENTION

Subsequently described are the inventions possible embodiments with references to figures. To an expert in the field it will clear from this description that the following preferred embodiments of the invention are meant only for figures and not with the intent of limiting the invention.

Figure 1:
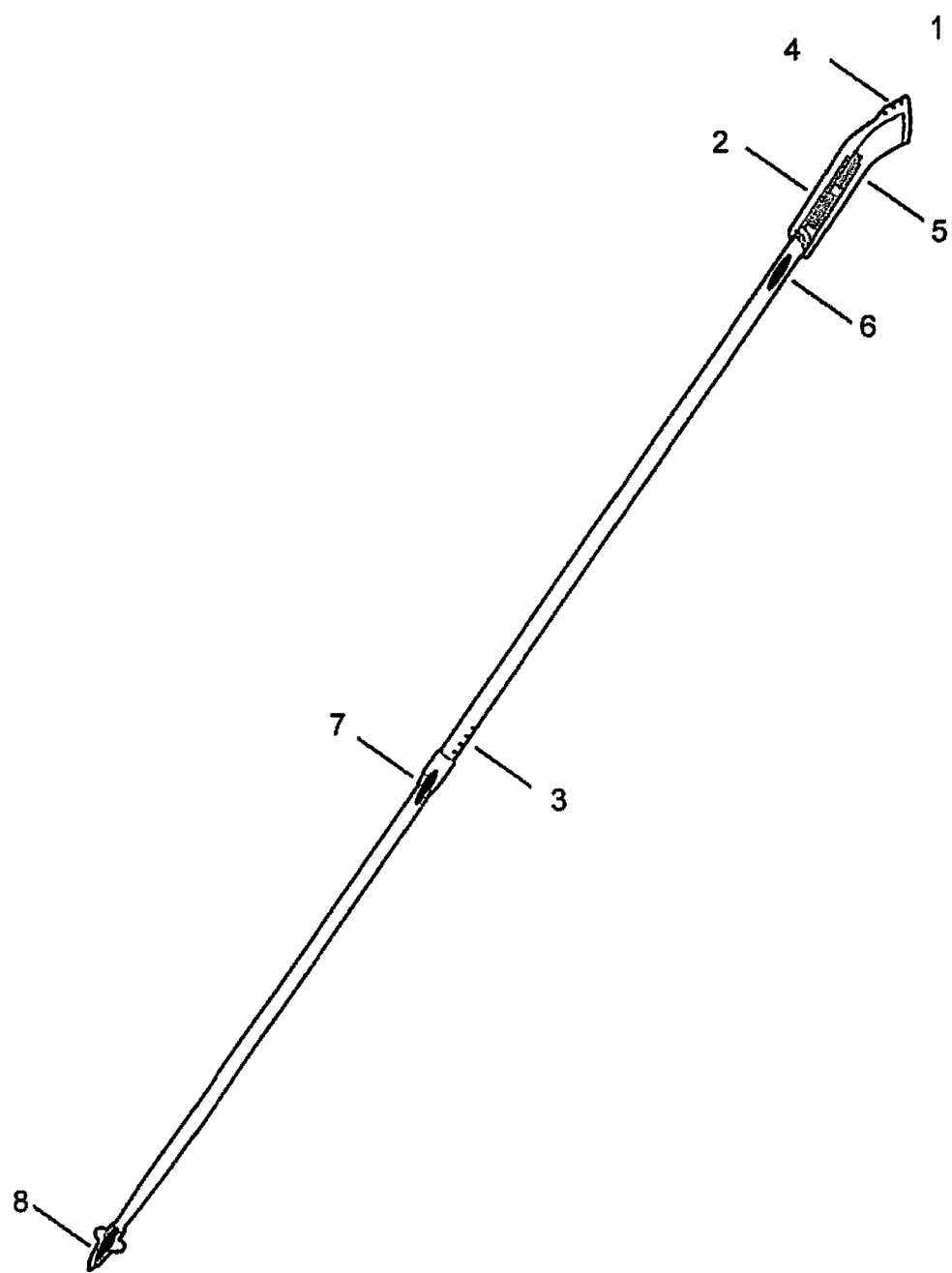
FIG. 1 shows a graphic representation of the invention's preferred embodiment with the elements used in the invention.

FIG. 1 shows a sport pole 1 according to the invention, installed into which is a sports' technique and execution analysing control center 2 and sensors, corresponding to the sports' execution, measuring physical and geodetic values, along with signal lights 3 and 4, all of which get energy from a battery 5 located in the sport pole handle. The sport pole 1 can be both adjustable or unadjustable, also known as a one-piece as is known to experts of the field.

The aforementioned sensors measuring physical and geodetic values are the inclination sensor 6, located near the handle, the pole length sensor 7, located at the bottom of the pole, the force sensor 8, located in the sport pole's lower end, which is in either direct or secondary (via the pole tip) contact with the ground and a GPS receiver 9 (coupled with topographical maps) located near the handle (or in an external device e.g. smart phone, watch etc.).

Figure 2:
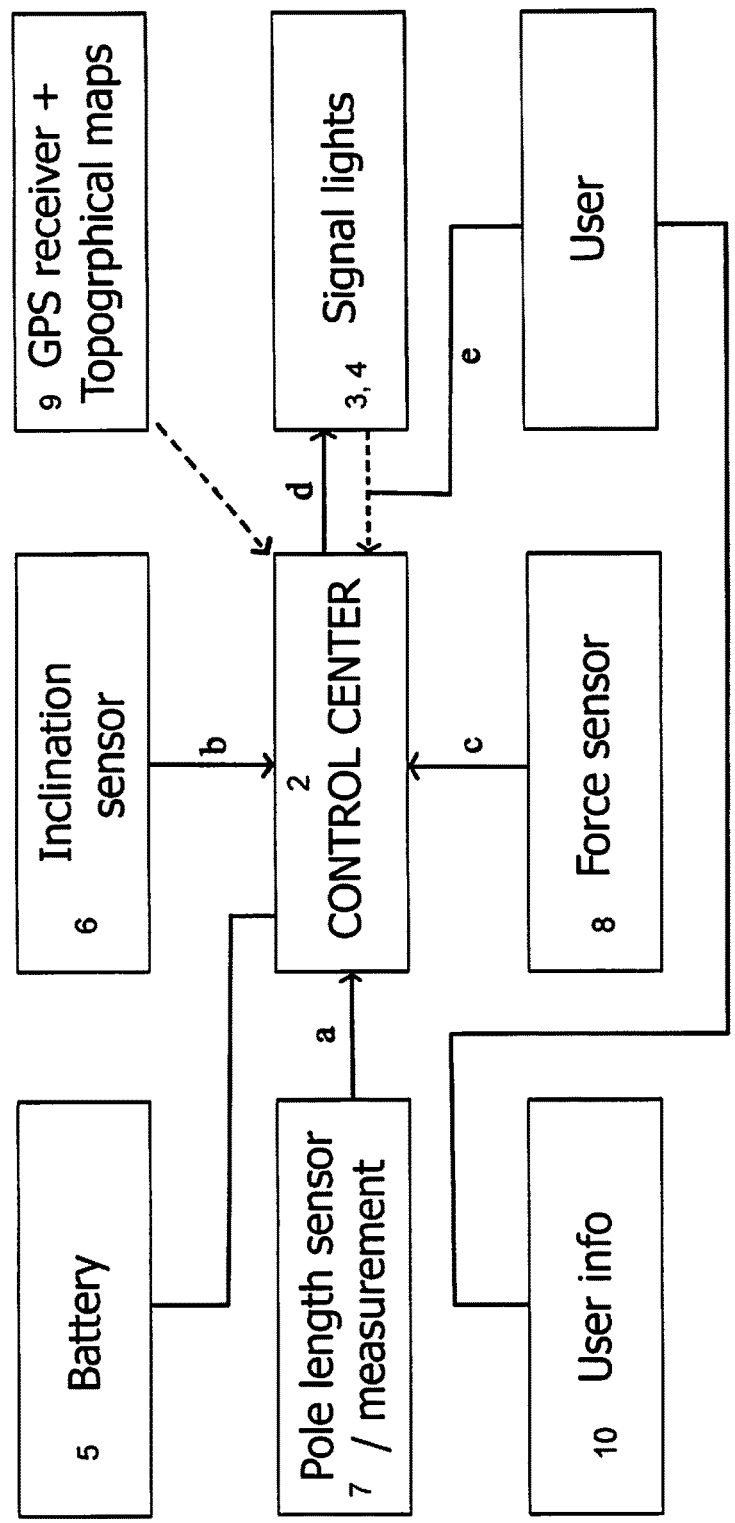
FIG. 2 shows a diagram of the elements in the invention and their functions.

FIG. 2 shows the control center's 2, inside the sport pole 1, data gathering, analysing and result communication to the user via signal lights. The control center 2 will presumably include common computer parts such as a casing to house everything, an info input and output interface, a mainboard with expansion slots, a power supply and storage devices such as a hard disk. The storage devices will include programs and user info that the control center uses and results it reaches. Through the input interface or mainboard expansion cards the sport pole 1 also has access to e.g. a GPS receiver 9, a compass, a WiFi adapter, a Blue Tooth adapter and an external power supply.

In the following explanations using the sport poles' 1 for nordic walking has been taken as an example. The control center 2 starts gathering data from the pole length sensor. The pole length sensor is presumably digital, removing the need for manual pole length input, however it can also be a combination of a measuring scale on the pole and an input interface, where the user manually inputs the pole length into the control center's system (like a person inputs data into a computer via a keyboard) or any other solution that fulfills the same objective.

Next the inclination sensor comes into use, which determines the poles inclination in relation to the ground. Using GPS the control center first compares the poles inclination with a topographical map to understand how ground inclination is affecting the inclination sensor's readings. Subsequently the inclination sensor compares the poles average inclination range, meaning the pole inclination in relation to the ground from the start of a push to the end of it, with its premade model. If the user's activity model differs significantly from the control center's premade model the control center compares the user's height, age and trauma history with the pole length and signals the user of the need for pole adjustment and direction (shorter or longer) with signal lights. In place of signal lights the same function can be filled with vibrations, sounds, a small display (LCD, hologram etc) attached to the pole, a real-time wirelessly connected picture in a smart device or a combination of the afore mentioned systems or other systems fulfilling the same ultimate goal.

The force sensor comes into use when prior indicators are okay, because otherwise the force sensor's measurements are incorrect due to incorrect pole length, unequal pole length or wrong technique.

The control center contacts the force sensor after creating a user force application model corresponding to the user info. During walking the control center will get data about the force a user is applying to propel themselves forward through the force sensor's measurements. Depending on a person's user info they must propel 5-40% of their body mass forward. At the same time the force sensor enables to measure the upper-body Sagittal plane strength balance, meaning to compare the left side torso and hand activity with the right side torso and hand activity. This opens up the possibility of adjusting the sport poles individually to even the upper-body Sagittal plane strength balance and train the sides at different intensity levels. This attribute is especially important when speaking about nordic walking in a rehabilitation context, where a person's movements are affected by temporary or permanent physical trauma(s).

Because the sport pole uses several electronic devices for data measuring, analysis and user communication, then naturally the invention also includes an energy supplying element like a battery to provide electricity for the devices, but also all other solutions fulfilling the same purpose, and a means to recharge such an element, e.g. a USB port. Considering however that this is a mobile exercise tool used mainly outdoors, then there exists a number of opportunities to tie this invention with electricity producing elements such as solar batteries or physical energy, e.g. friction/pressure, to electricity converting elements. A combination of the priorly mentioned elements may also be used to fully or partly cover the invention's energy need.

Figure 4:
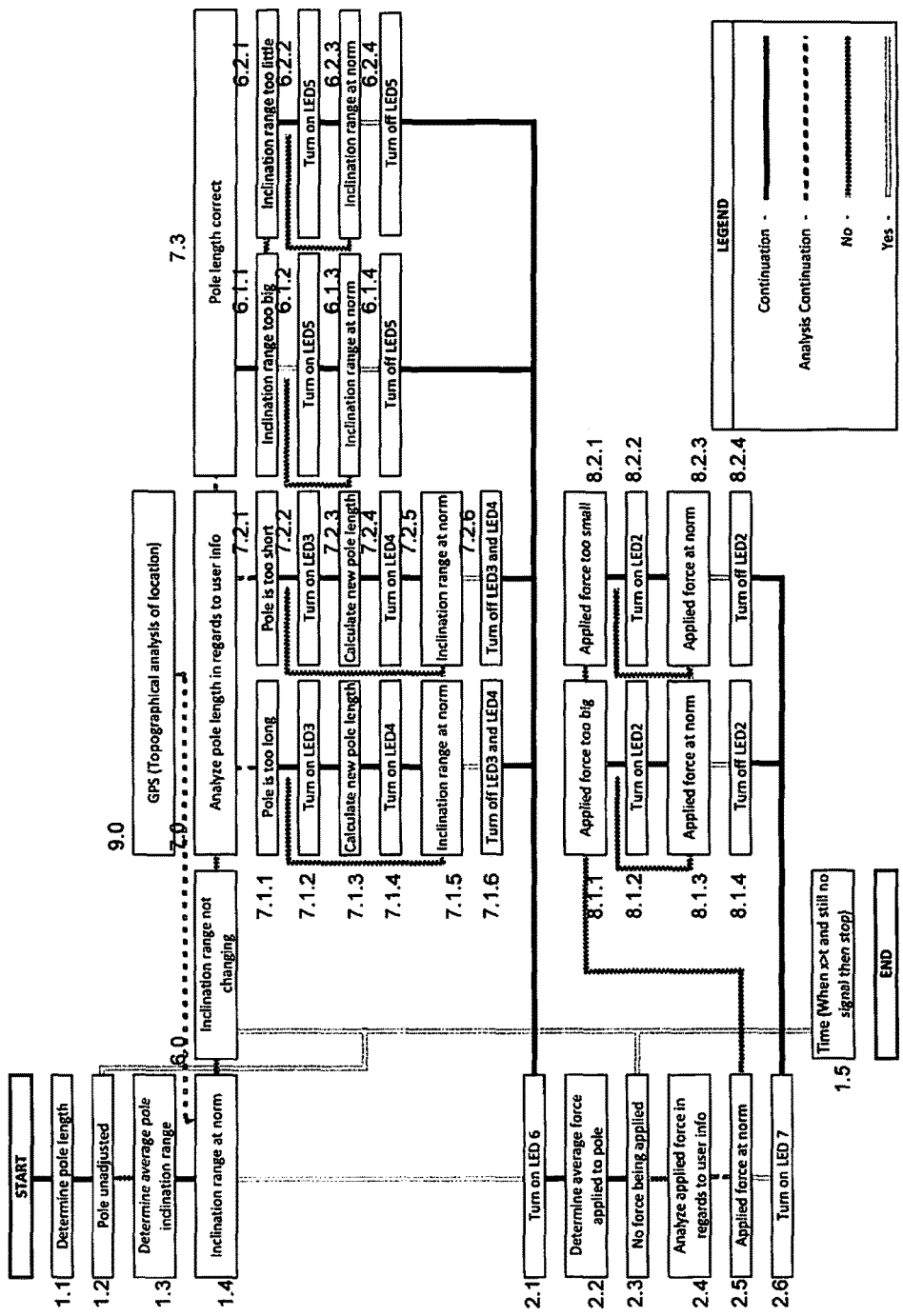
FIG. 4 shows an example of the control center's work process when the pole is in use.

FIG. 3 shows a table explaining the meaning of the signal lights used in FIG. 4.

FIG. 4 shows a logic scheme, which features one possible working example of the invention in repeated use. This means that a user has already input and saved their user info earlier. Shown is the control center's operation, communication with other sensors and communication with the user via signal lights. In the given example the operation process begins from the sport pole pole length measurement, where the control center has activated, because the user has signalled the impending use of the sport poles by pushing the start button. Alternatively the start button may be replaced by the pole tips being banged on the ground or another solution like a voice command. To conserve energy the control center examines whether the poles have been adjusted for usage. If the sport poles adjustment has not been started in a given time frame then the control center will automatically cancel the session.

If the sport poles have been adjusted into position or already being used 4 1.1 until 1.2, the control center can analyse the average pole inclination range through the inclination sensor 1.3 until 1.4 At the same time the control center monitors the user's location and with the assistance of a topographical map is able to consider the factors affecting the pole inclination range due to ground inclination. If the inclination range differs significantly from the premade model, then the control center will request the person's height, trauma history and age from its memory, which it then compares to the pole length received from the pole length sensor. During this analysis 7.1.1 until 7.2.6 the control center will understand if the user's exercise tool is fitting for their anthropometric measurements. If for example the sport pole is too long, then it will let the user know, as shown in FIG. 3, by lighting the signal light at the tip of the pole, LED 3 FIG. 4 and computes a new pole length. The sport pole will show the new pole length on the pole adjustment scale, lighting the signal light on the LED 4 light strip, which equals to the new pole length received from the computation result.

On FIG. 4 it is seen that only after the pole length and inclination check, processes 6.0, 7.0, 7.1.1 until 7.2.6, 7.3, 6.1.1 until 6.2.4 does the control center take contact with the force sensor, processes 8.1.1 until 8.2.4. This is because it guarantees uniquely interpretable readings that are no longer affected by wrong technique, a deviation from the optimal force application pole inclination range or unequal sport poles' length. It is important to note that the inclination range and with it the ground inclination control do not stop, but continues consistently during further analysis. Subsequently the control center starts sending constant inquiries to the force sensor about the user's average force application processes 2.1 until 2.6 and at the same time to the memory about the user's user info. By analyzing the average force application and user info, the pole figures out whether the user needs to apply more or less force to propel themselves forward, so the exercise would stimulate the body, whilst bearing minimum overload risk and considering any traumas affecting the person.

If force application is at norm, then the sport pole will let the user know by turning on the signal light LED 7. Like before the force sensor data collection and analysis will also continue consistently until discord emerges between the inclination range premade model and activity model or the usage of sport poles ends.

It is important to understand that the communication between the different elements in the sport pole is not limited to, but will presumably work via wireless communication like Blue Tooth. This decreases extra wiring and pole weight and durability problems derived from it. At the same time it also allows the control center to be moved to just one pole or out of the pole completely into e.g. a smart device or computer.

Figure 5:
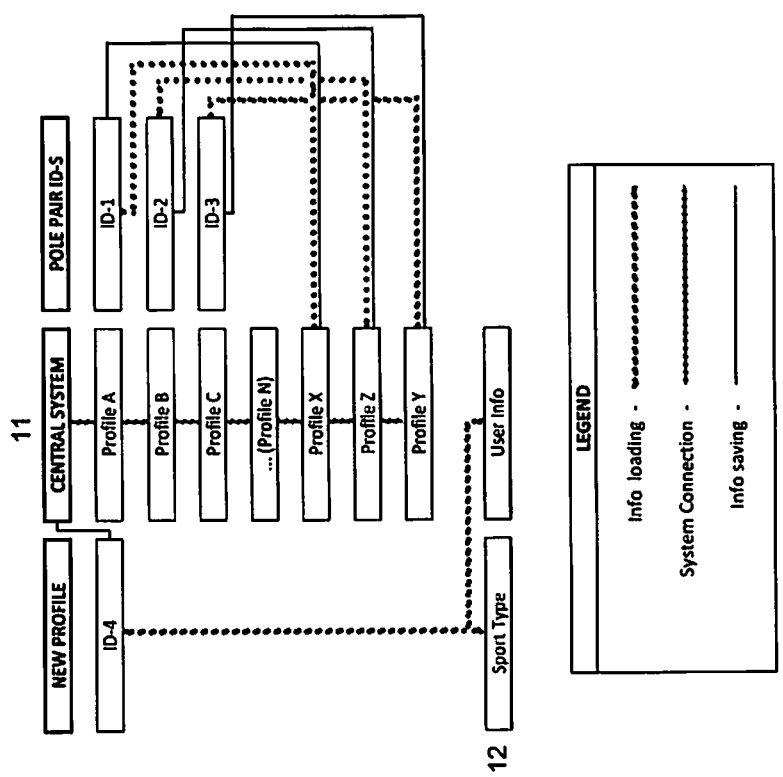
FIG. 5 shows and example solution to problems arising from shared pole use due to different user info.

The usage of the same training tools by different users figure FIG. 5 profiles A until Y and the resulting completely different user info and sport problem is solved by the so-called "new player" system. Just like in computer games where the player can create a new account or character every new user creates a new profile before using the sport poles. During profile creation the necessary user info and sport is input, which allows easy user and sport change. In schools, rehabilitation or training centers and other establishments where one pole pair has many potential users the same system can be expanded as is explained in figure FIG. 5. The user profiles are recorded into one central system and the sport poles are given unique digital ID-s. In the given example X profile is uploaded onto ID-1 sport poles, Y profile onto ID-2 sport poles and Z profile onto ID-3 sport poles. After usage the recorded data is uploaded back into the central system and the sport poles are ready to be used again, however the information recorded onto the profiles can be viewed and analyzed in the central system regardless of that.

The invention claimed is:

1. A sport's pole, comprising:
   a pole having a ground contacting end, a handle end, and a length which extends from the ground contacting end to the handle;
   at least one inclination sensor which senses an incline of the pole;
   at least one force sensor which senses a force applied by the ground contacting end against a surface;
   a controller which receives sensor information from the at least one inclination sensor and the at least one force sensor,
   wherein the controller is preprogrammed with one or more force application models which have a specified range of model performance parameters based on at least each of the length of the pole, the incline of the pole, and the force applied,
   wherein the controller determines one or more performance parameters based on information provided by the at least one inclination sensor, the at least one force sensor, and information pertaining to the length of the pole, and whether the one or more performance parameters are within the specified range of model performance parameters; and
   a signaling device operably connected to the controller to provide signals indicating whether the one or more performance parameters are within or not within the specified range of model performance parameters.

2. The sport's pole of claim 1 further comprising a global positioning system (GPS) associated with the pole for determining a geographical location of the pole, and wherein the controller is configured to access stored topographical information, and wherein the specified range of model performance parameters determined by the controller using the one or more force application models is adjustable depending on topographical information for the geographical location of the pole determined by the GPS.

3. The sport's pole of claim 2 wherein the GPS and the controller are in a handle at the handle end of the pole.

4. A method for using a sport's pole according to claim 2, comprising:
   repetitively contacting the surface with the ground contacting end of the pole and applying a force;
   determining the one or more parameters using the controller based on the repetitive contacting; and
   signaling whether the one or more performance parameters are within or not within the specified range of model performance parameters.

5. The sport's pole of claim 1 wherein said controller is configured to receive anthropometric measurements of one or more user's, and wherein the specified range of model performance parameters determined by the controller using the one or more force application models is adjustable depending on the received anthropometric measurements.

6. The sport's pole of claim 5 wherein the length of the pole is adjustable, and wherein said controller is configured to cause said signaling device to provide a signal to adjust a length of the pole based on the one or more performance parameters determined by the controller.

7. A method for using a sport's pole according to claim 5, comprising:
   repetitively contacting the surface with the ground contacting end of the pole and applying a force;

determining the one or more parameters using the controller based on the repetitive contacting; and signaling whether the one or more performance parameters are within or not within the specified range of model performance parameters.

8. The method of claim 7 further comprising signaling to make an adjustment to the length of the pole.

9. The sport's pole of claim 1 wherein the length of the pole is adjustable.

10. The sport's pole of claim 9 further comprising a length sensor for sensing the length of the pole, and wherein said controller receives signals from the length sensor indicative of the length of the pole.

11. The sport's pole of claim 10 wherein said controller is configured to cause said signaling device to provide a signal to adjust a length of the pole based on the one or more performance parameters.

12. The sport's pole of claim 1 further comprising a battery for providing power to at least one of the controller, the at least one force sensor, the at least one incline sensor.

13. The sport's pole of claim 12 wherein said battery is a re-chargeable battery or a solar powered battery.

14. The sport's pole of claim 1 wherein the signaling device includes one or more lights.

15. The sport's pole of claim 14 wherein the one or more lights are light emitting devices.

16. The sport's pole of claim 1 wherein the signaling device is a vibratory device.

17. The sport's pole of claim 1 wherein the signaling device provides a signal by a wireless communication.

18. The sport's pole of claim 1 wherein the controller is configured for wireless communication.

19. A method for using at least one sport pole having an adjustable length and a control center configured to sense and analyze force, inclination, pole length, user information and topological information, comprising the steps of inputting into the control center said user information selected from the group consisting of age, weight, height, fitness level, limb strength differences, right and left upper-body sagittal plane strength or balance, trauma history, temporary or permanent impairment due to trauma and training goals, and a predetermined user force application model for a user, determining a starting pole length for said at least one sport pole, applying force to said at least one sport pole during walking, gathering data in the control center regarding said force, inclination and starting pole length, analyzing and comparing said data to said predetermined user force application model, and determining that said starting pole length of said at least one sport pole is appropriate for said user, or indicating that said starting pole length needs to be adjusted to a shorter or longer length.

20. The method of claim 19, wherein said user is using two sport poles, comprising the further steps of identifying differences in said right and left upper-body sagittal plane strength or balance, and adjusting a first sport pole differently from an adjustment that may be made to a second sport pole to accommodate said differences.

* * * * *